United States Patent [19]

Macor et al.

[11] Patent Number: 5,747,501

[45] Date of Patent: May 5, 1998

[54] INDOLE DERIVATIVES

[75] Inventors: John Eugene Macor, Salem, Conn.; Martin James Wythes, Sutton, United Kingdom

[73] Assignee: Pfizer, Inc., New York, N.Y.

[21] Appl. No.: 295,798

[22] PCT Filed: Mar. 10, 1993

[86] PCT No.: PCT/US93/01967

§ 371 Date: Sep. 16, 1994

§ 102(e) Date: Sep. 16, 1994

[87] PCT Pub. No.: WO93/20073

PCT Pub. Date: Oct. 14, 1993

Related U.S. Application Data

[63] Continuation-in-part of Ser. No. 864,737, Apr. 7, 1992.

[51] Int. Cl.[6] .................. A61K 31/40; C07D 413/14
[52] U.S. Cl. ................. 514/376; 514/339; 514/340; 514/341; 514/342; 514/369; 514/386; 514/389; 514/397; 514/415; 546/269.7; 546/271.4; 546/277.1; 548/182; 548/183; 548/226; 548/229; 548/231; 548/232; 548/312.1; 548/467; 548/504; 548/543
[58] Field of Search ............... 514/376; 548/226, 548/229, 231

[56] References Cited

U.S. PATENT DOCUMENTS

| | | | |
|---|---|---|---|
| 4,252,803 | 2/1981 | Webb. | |
| 4,689,336 | 8/1987 | Schnur | 514/376 |
| 4,806,655 | 2/1989 | Wagnon | 548/231 |
| 4,839,377 | 6/1989 | Bays et al. | 514/415 |
| 4,855,314 | 8/1989 | Oxford et al. | 514/415 |
| 4,968,707 | 11/1990 | Clark et al. | 514/376 |
| 5,208,248 | 5/1993 | Baker et al. | 514/364 |
| 5,334,606 | 8/1994 | MacLeod | 514/376 |
| 5,399,574 | 3/1995 | Robertson et al. | 514/376 |

FOREIGN PATENT DOCUMENTS

| | | |
|---|---|---|
| 0303506 | 8/1988 | European Pat. Off. . |
| 0313397 | 10/1988 | European Pat. Off. . |
| 0354777 | 8/1989 | European Pat. Off. . |
| 0438230 | 7/1991 | European Pat. Off. . |
| 0497512 | 8/1992 | European Pat. Off. . |
| 9118897 | 12/1991 | WIPO . |

OTHER PUBLICATIONS

W. Feniuk, et al., P.P.A. Humphrey & M. J. Perren –Br. J. Pharmacol. (1989), 96, 83–90.

P. P. A. Humphrey, et al. –Br. J. Pharmacol. (1988), 94, 1123–1132.

R. E. Hearing, et al. *J. Neuroscience*, 7, 894 (1987).

*Primary Examiner*—Donald G. Daus
*Attorney, Agent, or Firm*—Peter C. Richardson; Paul H. Ginsburg; Grover F. Fuller, Jr.

[57] ABSTRACT

Compounds of the formula

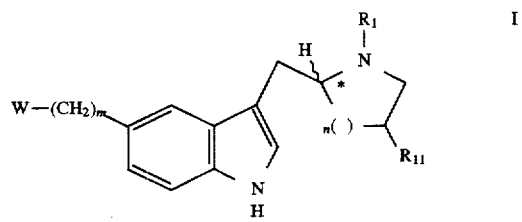

where W is

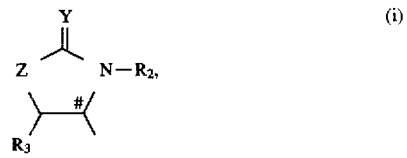 (i)

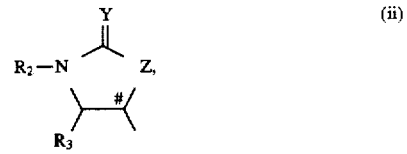

(ii)

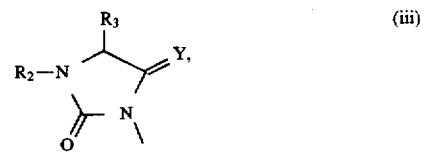

(iii)

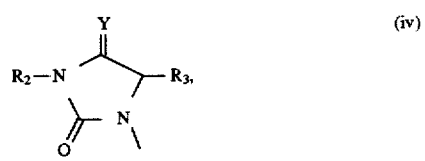

(iv)

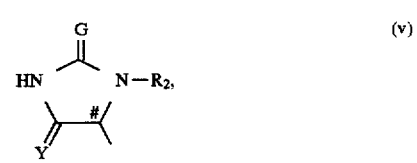

(v)

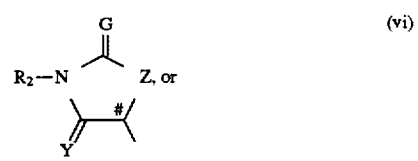

(vi)

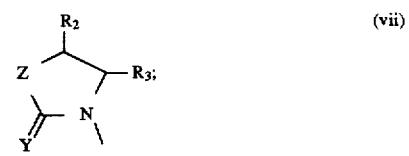

(vii)

n is 0, 1, or 2; m is 0, 1, 2, or 3; Y and G are each independently oxygen or sulfur; Z is —O—, —S—, —NH, or —CH$_2$; R$_1$ is hydrogen, C$_1$ to C$_8$ alkyl, substituted C$_1$ to C$_8$ alkyl substituted with one hydroxy, C$_3$ to C$_8$ alkenyl, C$_3$ to C$_8$ alkynyl, aryl, C$_1$ to C$_3$ alkylaryl, C$_1$ to C$_3$ alkylheteroaryl, or —Q—R$_4$; R$_2$ and R$_3$ are each independently hydrogen, $C_1$ to $C_6$ alkyl, aryl, $C_1$ to $C_3$ alkylaryl, or $C_1$ to $C_3$ alkylheteroaryl; $R_4$ is cyano, trifluoromethyl, $-COR_9$, $-CO_2R_9$, $-CONR_9R_{10}$, $-OR_9$, $-SO_2NR_9R_{10}$, or $-S(O)_qR_9$; $R_9$ and $R_{10}$ are each independently hydrogen, $C_1$ to $C_8$ alkyl, $C_1$ to $C_3$ alkylaryl, aryl, or $R_9$ and $R_{10}$ may together be taken to form a three- to seven-membered alkyl ring or a three- to seven-membered heteroalkyl ring having 1 heteroatom of O; Q is $C_1$ to $C_3$ alkyl; $R_{11}$ is hydrogen, $-OR_{12}$, or $-NHCOR_{12}$; $R_{12}$ is hydrogen, $C_1$ to $C_6$ alkyl, aryl, or $C_1$ to $C_3$ alkylaryl; q is 0, 1, or 2; a first chiral carbon is designated by an asterisk; a second chiral carbon is designated by #; and the above aryl groups and the aryl moieties of the above alkyl-aryl groups are independently selected from phenyl and substituted phenyl, wherein said substituted phenyl may be substituted with one to three groups selected from $C_1$ to $C_4$ alkyl, halogen, hydroxy, cyano, carboxamido, nitro, and $C_1$ to $C_4$ alkoxy, and the pharmaceutically acceptable salts thereof.

These compounds are useful in treating migraine and other disorders are new. These compounds are useful psychotherapeutics and are potent serotonin (5-$HT_1$) agonists and may be used in the treatment of depression, anxiety, eating disorders, obesity, drug abuse, cluster headache, migraine, pain, and chronic paroxysmal hemicrania and headache associated with vascular disorders, and other disorders arising from deficient serotonergic neurotransmission. The compounds can also be used as centrally acting antihypertensives and vasodilators.

22 Claims, No Drawings

INDOLE DERIVATIVES

This is a the national phase of application number PCT/US93/01967 which, in turn, is a continuation-in-part of U.S. patent application Ser. No. 07/864,737 filed on Apr. 7, 1992 from which priority is claimed from both applications.

BACKGROUND OF THE INVENTION

The present invention relates to indole derivatives, to processes and intermediates for their preparation, to pharmaceutical compositions containing them and to their medicinal use. The active compounds of the present invention are useful in treating migraine and other disorders.

U.S. Pat. Nos. 4,839,377 and 4,855,314 and European Patent Application Publication Number 313397 refer to 5-substituted 3-aminoalkyl indoles. The compounds are said to be useful for the treatment of migraine.

British Patent Application 040279 refers to 3-aminoalkyl-1H-indole-5-thioamides and carboxamides. The compounds are said to be useful in treating hypertension, Raymond's disease and migraine.

European Patent Application Publication Number 303506 refers to 3-poly:hydro-pyridyl-5-substituted-1H-indoles. The compounds are said to have 5-HT, receptor agonist and vasoconstrictor activity and to be useful in treating migraine.

European Patent Application Publication Number 354777 refers to N-piperidinyl:indolyl:ethyl-alkane sulfonamide derivatives. The compounds are said to have 5-HT$_1$ receptor agonist and vasoconstrictor activity and to be useful in treating cephalic pain.

European Patent Applications Publication Numbers 438230, 494774, and 497512 refers to indole-substituted five-membered heteroaromatic compounds. The compounds are said to have 5-HT$_1$-like receptor agonist activity and to be useful in the treatment of migraine and other disorders for which a selective agonist of these receptors is indicated.

International Patent Application PCT/GB91/00908 and European Patent Application No. 313397A refers to 5-heterocyclic indole derivatives. The compounds are said to exhibit properties useful in the treatment and prophylaxis of migraine, cluster headache, and headache associated with vascular disorders. These compounds are also said to have "5-HT$_1$-like" receptor agonism.

SUMMARY OF THE INVENTION

The present invention relates to compounds of the formula

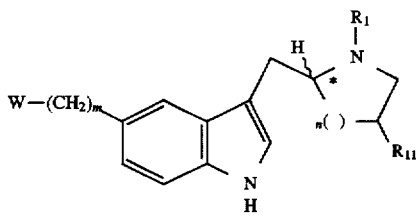

where W is

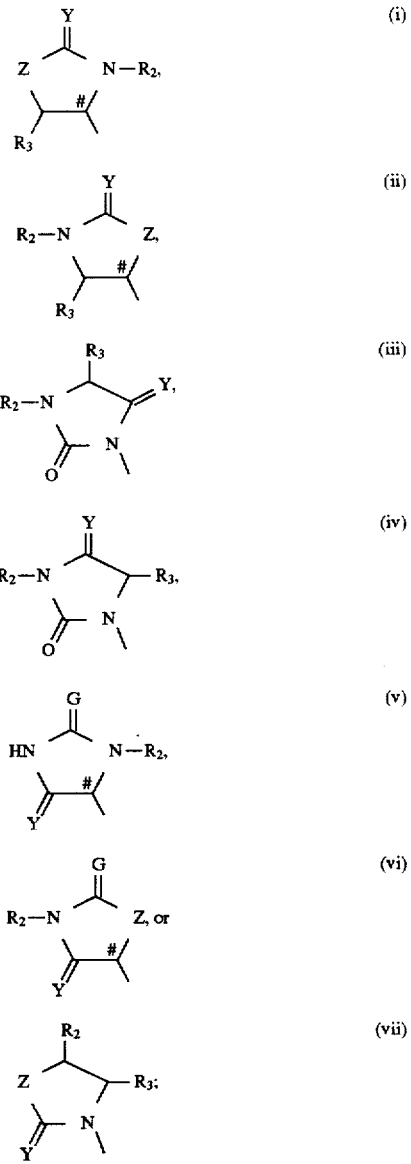

$n$ is 0, 1, or 2; $m$ is 0, 1, 2, or 3; Y and G are each independently oxygen or sulfur; Z is —O—, —S—, —NH, or —CH$_2$; R$_1$ is hydrogen, C$_1$ to C$_8$ alkyl, substituted C$_1$ to C$_8$ alkyl substituted with one hydroxy, C$_3$ to C$_8$ alkenyl, C$_3$ to C$_8$ alkynyl, aryl, C$_1$ to C$_3$ alkylaryl, C$_1$ to C$_3$ alkylheteroaryl, or —Q—R$_4$; R$_2$ and R$_3$ are each independently hydrogen, C$_1$ to C$_6$ alkyl, aryl, C$_1$ to C$_3$ alkylaryl, or C$_1$ to C$_3$ alkylheteroaryl; R$_4$ is cyano, trifluoromethyl, —COR$_9$, —CO$_2$R$_9$, —CONR$_9$R$_{10}$, —OR$_9$, —SO$_2$NR$_9$R$_{10}$, or —S(O)$_q$R$_9$; R$_9$ and R$_{10}$ are each independently hydrogen, C$_1$ to C$_8$ alkyl, C$_1$ to C$_3$ alkylaryl, aryl, or R$_9$ and R$_{10}$ may together be taken to form three- to seven-membered alkyl ring or a three- to seven-membered heteroalkyl ring having 1 heteroatom of O; R$_{11}$ is hydrogen, —OR$_{12}$, or —NHCOR$_{12}$; R$_{12}$ is hydrogen, C$_1$ to C$_6$ alkyl, aryl, or C$_1$ to C$_3$ alkyl-aryl; q is 0, 1, or 2; Q is C$_1$ to C$_3$ alkyl; a first chiral carbon is designated by an asterisk; a second chiral carbon is designated by #; and the above aryl groups and the aryl moieties of the above alkyl-aryl groups are independently selected from phenyl and substituted phenyl, wherein said substituted phenyl may be substituted with one to three groups selected from $C_1$ to $C_4$ alkyl, halogen (e.g., fluorine, chlorine bromine or iodine), hydroxy, cyano, carboxamido, nitro, and $C_1$ to $C_4$ alkoxy, and the pharmaceutically acceptable salts thereof. These compounds are useful in treating migraine and other disorders.

The compounds of the invention include all optical isomers of formula I (e.g., R and S stereogenicity at any chiral site) and their racemic, diastereomeric, or epimeric mixtures. The epimers with the S absolute configuration at the chiral carbon site designated by # in formula I are preferred. When $R_{11}$ is hydrogen, the epimers with the R absolute configuration at the chiral carbon site designated by an asterisk in formula I are preferred. When $R_{11}$ is —$OR_{12}$ or —$NHCOR_{12}$ and n is 0 or 1, the epimers with the S absolute configuration at the chiral carbon site designated by an asterisk in formula I are preferred. When $R_{11}$ is —$OR_{12}$ or —$NHCOR_{12}$ and n is 2, the epimers with the R absolute configuration at the chiral carbon site designated by an asterisk in formula I are preferred. When $R_{11}$ is —$OR_{12}$ or —$NHCOR_{12}$ and n is 0, the cis epimers [(2S, 3S) absolute configuration in the azetidine ring] are particularly preferred. When $R_{11}$ is —$OR_{12}$ or —$NHCOR_{12}$ and n is 1, the cis epimers [(2S, 4R) absolute configuration in the pyrrolidine ring] are particularly preferred. When $R_{11}$ is —$OR_{12}$ or —$NHCOR_{12}$ and n is 2, the cis epimers [(2R, 5R) absolute configuration in the piperidine ring] are particularly preferred.

Unless otherwise indicated, the alkyl, alkenyl, and alkynyl groups referred to herein, as well as the alkyl and alkylene moieties of other groups referred to herein (e.g. alkoxy), may be linear or branched, and they may also be cyclic (e.g. cyclopropyl, cyclobutyl, cyclopentyl, or cyclohexyl) or be linear or branched and contain cyclic moieties.

Preferred compounds of the invention are compounds of the formula I wherein W is (i), (ii), or (iii); n is 1; m is 1; $R_1$ is hydrogen, $C_1$ to $C_3$ alkyl, or —$CH_2CH_2OCH_3$; $R_2$ is hydrogen; and $R_3$ is hydrogen or —$CH_2Ph$ (Ph=phenyl). Of the foregoing preferred compounds, the epimers with the S optical configuration at the chiral carbon designated by # in formula I are more preferred. Of the foregoing preferred compounds, when $R_{11}$ is hydrogen, the epimers with the R absolute configuration at the chiral carbon site designated by an asterisk in formula I are more preferred. Of the foregoing preferred compounds, when $R_{11}$ is —$OR_{12}$ or —$NHCOR_{12}$, the epimers with the S absolute configuartion at the chiral carbon site designated by an asterisk in formula I are more preferred. Of the foregoing compounds, when $R_{11}$ is —$OR_{12}$ or —$NHCOR_{12}$, the cis epimers [(2S, 4R) absolute configuration in the pyrrolidine ring] are particularly preferred.

The following compounds are particularly preferred:

3-[(N-2-Methoxyethyl)pyrrolidin-2R-ylmethyl]-5-(2-oxo-1,3-oxazolidin-4S-ylmethyl)-1H-indole;

5-(2-Oxo-1,3-oxazolidin-4S-ylmethyl)-3-(pyrrolidin-2R-ylmethyl)-1H-indole; and 3-(N-Methylpyrrolidin-2R-ylmethyl)-5-(2-oxo-1,3-oxazolidin-4R,S-ylmethyl)-1H-indole.

The present invention also relates to a pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound of the formula I or a pharmaceutically acceptable salt thereof effective in treating such condition and a pharmaceutically acceptable carrier.

The present invention also relates to a method for treating a condition selected from hypertension, depression, anxiety, eating disorders, obesity, drug abuse, cluster headache, migraine, pain and chronic paroxysmal hemicrania and headache associated with vascular disorders comprising administering to a mammal (e.g., a human) requiring such treatment an amount of a compound of the formula I or a pharmaceutically acceptable salt thereof effective in treating such condition.

The present invention also relates to a pharmaceutical composition for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a method for treating disorders arising from deficient serotonergic neurotransmission (e.g., depression, anxiety, eating disorders, obesity, drug abuse, cluster headache, migraine, pain and chronic paroxysmal hemicrania and headache associated with vascular disorders) comprising administering to a mammal (e.g., a human) requiring such treatment an amount of a compound of the formula I or a pharmaceutically acceptable salt thereof effective in treating such condition.

The present invention also relates to a compound of the formula

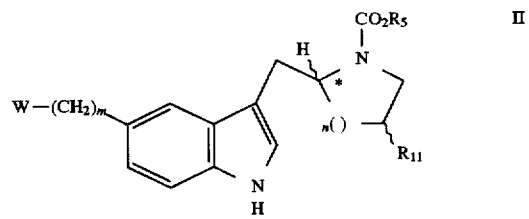

where W is

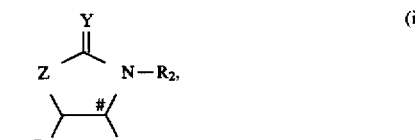

(i)

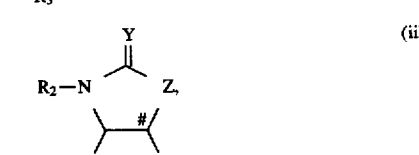

(ii)

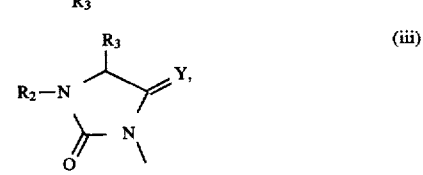

(iii)

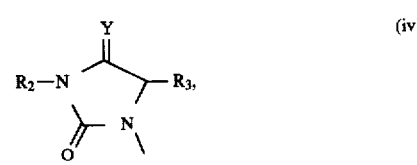

(iv)

-continued

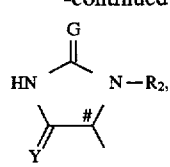
(v)

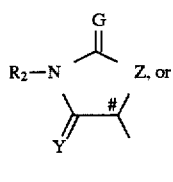
(vi)

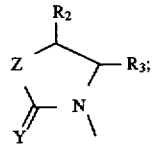
(vii)

n is 0, 1, or 2; m is 0, 1, 2, or 3; Y and G are each independently oxygen or sulfur; Z is —O—, —S—, —NH, or —CH$_2$; R$_2$ and R$_3$ are each independently hydrogen, C$_1$ to C$_6$ alkyl, aryl, C$_1$ to C$_3$ alkylaryl, and C$_1$ to C$_3$ alkylheteroaryl; R$_5$ is C$_1$ to C$_6$ alkyl, aryl, or C$_1$ to C$_3$ alkylaryl (preferably benzyl); R$_{11}$ is hydrogen, —OR$_{12}$, or —NHCOR$_{12}$; R$_{12}$ is hydrogen, C$_1$ to C$_6$ alkyl, aryl, or C$_1$ to C$_3$ alkyl-aryl; a first chiral carbon is designated by an asterisk; a second chiral carbon is designated by #; and the above aryl groups and the aryl moieties of the above alkyl-aryl groups are independently selected from phenyl and substituted phenyl, wherein said substituted phenyl may be substituted with one to three groups selected from C$_1$ to C$_4$ alkyl, halogen (e.g. fluorine, chlorine bromine or iodine), hydroxy, cyano, carboxamido, nitro, and C$_1$ to C$_4$ alkoxy. The epimers with the S absolute configuration at the chiral carbon site designated by # in formula II are preferred. When R$_{11}$ is hydrogen, the epimers with the R absolute configuration at the chiral carbon site designated by an asterisk in formula II are preferred. When R$_{11}$ is —OR$_{12}$ or —NHCOR$_{12}$ and n is 0 or 1, the epimers with the S absolute configuration at the chiral carbon site designated by an asterisk in formula II are preferred. When R$_{11}$ is —OR$_{12}$ or —NHCOR$_{12}$ and n is 2, the epimers with the R absolute configuration at the chiral carbon site designated by an asterisk in formula II are preferred. When R$_{11}$ is —OR$_{12}$ or —NHCOR$_{12}$ and n is 0, the cis epimers [(2S, 3S) absolute configuration in the azetidine ring] are particularly preferred. When R$_{11}$ is —OR$_{12}$ or —NHCOR$_{12}$ and n is 1, the cis epimers [(2S, 4R) absolute configuration in the pyrrolidine ring] are particularly preferred. When R$_{11}$ is —OR$_{12}$ or —NHCOR$_{12}$ and n is 2, the cis epimers [(2R, 5R) absolute configuration in the piperidine ring] are particularly preferred. The compounds of formula II are useful as intermediates in preparing compounds of formula I.

The present invention also relates to a compound of the formula

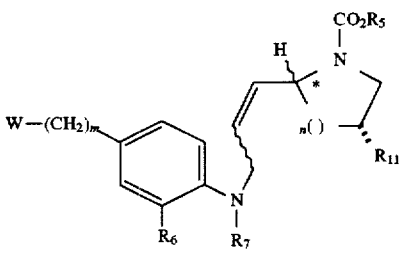
III where W is

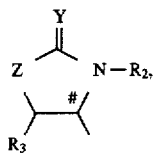
(i)

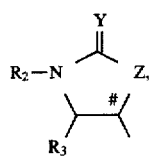
(ii)

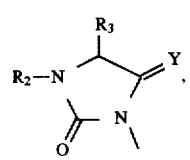
(iii)

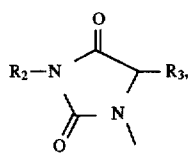
(iv)

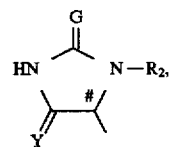
(v)

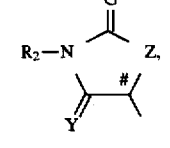
(vi)

or

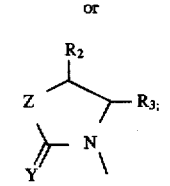
(vii)

n is 0, 1, or 2; m is 0, 1, 2, or 3; Y and G are each independently oxygen or sulfur; Z is —O—, —S—, —NH, or —CH$_2$; R$_2$ and R$_3$ are each independently hydrogen, C$_1$ to C$_6$ alkyl, aryl, C$_1$ to C$_3$ alkylaryl, or C$_1$ to C$_3$ alkylheteroaryl; R$_5$ is C$_1$ to C$_6$ alkyl, aryl, or C$_1$ to C$_3$ alkylaryl (preferably benzyl); R$_6$ is halogen [preferably bromide]; R$_7$ is —COCF$_3$, —SO$_2$CH$_3$, —SO$_2$Ph, or —CO$_2$C(CH$_3$)$_3$; R$_{11}$ is hydrogen, —OR$_{12}$, or —NHCOR$_{12}$; R$_{12}$ is hydrogen, C$_1$ to C$_6$ alkyl, aryl, or C$_1$ to C$_3$ alkyl-aryl; a first chiral carbon is designated by an asterisk; a second chiral carbon is designated by #; and the above aryl groups and the aryl moieties of the above alkyl-aryl groups are independently selected from phenyl and substituted phenyl, wherein said substituted phenyl may be substituted with one to three groups selected from C$_1$ to C$_4$ alkyl, halogen (e.g. fluorine, chlorine bromine or iodine), hydroxy, cyano, carboxamido, nitro, and C$_1$ to C$_4$ alkoxy. The epimers with the S absolute configuration at the chiral carbon site designated by # in formula III are preferred. When R$_{11}$ is hydrogen, the epimers with the R absolute configuration at the chiral carbon site designated by an asterisk in formula III are preferred. When R$_{11}$ is —OR$_{12}$ or —NHCOR$_{12}$ and n is O or 1, the epimers with the S absolute configuration at the chiral carbon site designated by an asterisk in formula III are preferred. When R$_{11}$ is —OR$_{12}$ or —NHCOR$_{12}$ and n is 2, the epimers with the R absolute configuration at the chiral carbon site designated by an asterisk in formula III are preferred. When R$_{11}$ is —OR$_{12}$ or —NHCOR$_{12}$ and n is O, the cis epimers [(2S, 3S) absolute configuration in the azetidine ring] are particularly preferred. When R$_{11}$ is —OR$_{12}$ or —NHCOR$_{12}$ and n is 1, the cis epimers [(2lS, 4R) absolute configuration in the pyrrolidine ring] are particularly preferred. When R$_{11}$ is —OR$_{12}$ or —NHCOR$_{12}$ and n is 2, the cis epimers [(2R, 5R) absolute configuration in the piperidine ring] are particularly preferred. The compounds of formula III are useful as intermediates in preparing compounds of formula II.

The present invention also relates to a compound of the formula

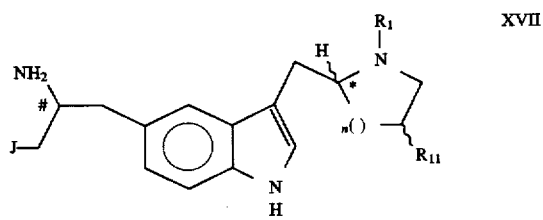

n is 0, 1, or 2; J is —OH or —CO$_2$R$_{13}$; R$_1$ is hydrogen, C$_1$ to C$_8$ alkyl, substituted C$_1$ to C$_8$ alkyl substituted with one hydroxy, C$_3$ to C$_8$ alkenyl, C$_3$ to C$_8$ alkynyl, aryl, C$_1$ to C$_3$ alkylaryl, C$_1$ to C$_3$ alkylheteroaryl, or —Q—R$_4$; R$_4$ is cyano, trifluoromethyl, —COR$_9$, —CO$_2$R$_9$, —CONR$_9$R$_{10}$, —OR$_9$, —SO$_2$NR$_9$R$_{10}$, or —S(O)$_q$R$_9$; R$_9$ and R$_{10}$ are each independently hydrogen, C$_1$ to C$_8$ alkyl, C$_1$ to C$_3$ alkylaryl, aryl, or R$_9$ and R$_{10}$ may together be taken to form a three- to seven-membered alkyl ring or a three- to seven-membered heteroalkyl ring having 1 heteroatom of O; R$_{11}$ is hydrogen, —OR$_{12}$, or —NHCOR$_{12}$; R$_{12}$ is hydrogen, C$_1$ to C$_6$ alkyl, aryl, or C$_1$ to C$_3$ alkyl-aryl; R$_{13}$ is C$_1$ to C$_6$ alkyl, aryl, or C$_1$ to C$_3$ alkyl-aryl; q is 0, 1, or 2; Q is C$_1$ to C$_3$ alkyl; a first chiral carbon is designated by an asterisk; and the above aryl groups and the aryl moieties of the above alky-aryl groups are independently selected from phenyl and substituted phenyl, wherein said substituted phenyl may be substituted with one to three groups selected from C$_1$ to C$_4$ alkyl, halogen, hydroxy, cyano, carboxamido, nitro, and C$_1$ to C$_4$ alkoxy. The epimers with the S absolute configuration at the chiral carbon site designated by # in formula XIV are preferred. When R$_{11}$ is hydrogen, the epimers with the R absolute configuration at the chiral carbon site designated by an asterisk in formula XIV are preferred. When R$_{11}$ is —OR$_{12}$ or —NHCOR$_{12}$ and n is O or 1, the epimers with the S absolute configuration at the chiral carbon site designated by an asterisk in formula XIV are preferred. When R$_{11}$ is —OR$_{12}$ or —NHCOR$_{12}$ and n is 2, the epimers with the R absolute configuration at the chiral carbon site designated by an asterisk in formula XIV are preferred. When R$_{11}$ is —OR$_{12}$ or —NHCOR$_{12}$ and n is O, the cis epimers [(2S, 3S) absolute configuration in the azetidine ring] are particularly preferred. When R$_{11}$ is —OR$_{12}$ or —NHCOR$_{12}$ and n is 1, the cis epimers [(2S, 4R) absolute configuration in the pyrrolidine ring] are particularly preferred. When R$_{11}$ is —OR$_{12}$ or —NHCOR$_{12}$ and n is 2, the cis epimers [(2R, 5R) absolute configuration in the piperidine ring] are particularly preferred. The compounds of formula XIV are useful as intermediates in preparing compounds of formula XVII.

DETAILED DESCRIPTION OF THE INVENTION

The compounds of the present invention are prepared via the following reaction scheme.

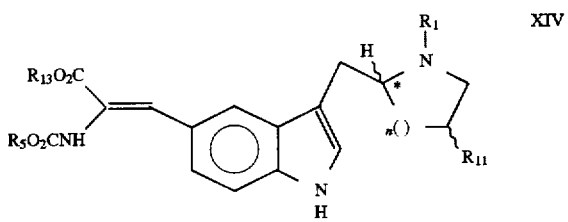

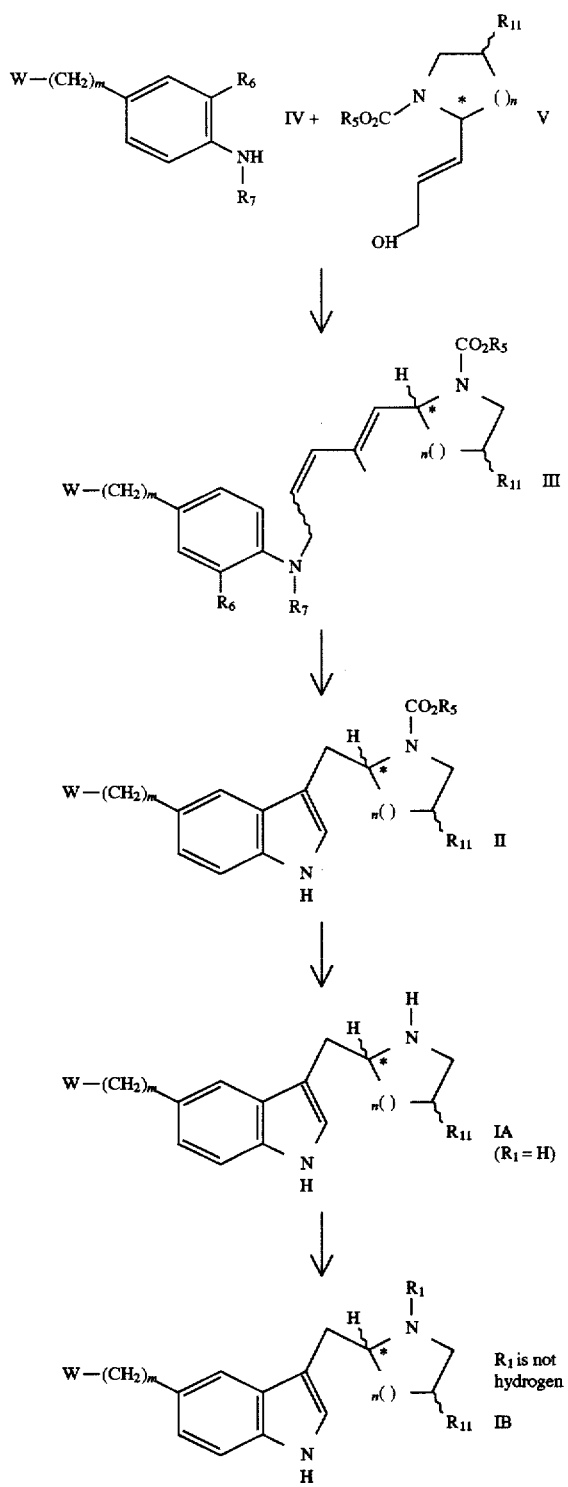

Suitable solvents include methylene chloride, ethers, (tetrahydrofuran, diethyl ether, and 1,4-dioxane), N,N-dimethylformamide and acetonitrile. The preferred solvent is tetrahydrofuran. The reaction is conducted at a temperature of from about 0° C. to about 65° C., most preferably at about 25° C.

Compounds of formula II can be prepared by the transition metal catalyzed cyclization of compounds of the formula III, wherein W, n, m, $R_5$, $R_6$ (preferably bromine or iodine), and $R_7$ (preferably trifluoroacetyl [—$COCF_3$]) and $R_{11}$ are as defined above, in a suitable inert solvent with a phase transfer catalyst and a base. Suitable transition metal catalysts include palladium salts such as palladium (II) acetate or palladium (II) chloride and rhodium salts, such as tris(triphenyl)rhodium (I) chloride. The preferred catalyst is palladium (II) acetate. Suitable solvents include N,N-dimethylformamide, acetonitrile, and N-methylpyrrolidinone. The preferred solvent is N,N-dimethylformamide. Suitable phase transfer catalysts include tetraalkylammonium halides, preferably tetra-n-butylammonium chloride. Suitable bases include tertiary amines, sodium hydrogen carbonate, and sodium carbonate. The preferred base is triethylamine. The reaction is conducted at a temperature of from about 60° C. to about 180° C., preferably from about 80° C. to about 100° C.

Compounds of formula IA wherein $R_1$ is hydrogen are prepared by catalytic reduction of a compound of the formula II, wherein W, n, m, and $R_5$ are as defined above. $R_5$ is preferably benzyl, under an atmosphere of hydrogen, preferably at a pressure of from about 1 to about 3 atmospheres, or using a hydrogen source such as ammonium formate or formic acid in an inert solvent. Suitable catalysts include palladium on carbon, Raney nickel, and platinum oxide. The preferred catalyst is palladium on carbon. Suitable solvents include $C_1$ to $C_6$ alcohols, N,N-dimethylformamide, ethyl acetate, and acetonitrile. The preferred solvent is ethanol. The reaction is conducted at a temperature of from about 0° C. to about 60° C., preferably about 25° C.

Compounds of formula IB wherein $R_1$ is not hydrogen can be prepared by the alkylation of a compound of formula IA wherein $R_1$ is hydrogen, and W, n, and m are as defined above with an alkylating agent of the formula $R_1$—LG and a base in an inert solvent, where LG is a suitable leaving group and $R_1$ is as defined above except for hydrogen. Examples of suitable leaving groups include —I, —Br, —Cl, —$OSO_2Ph$, —$OSO_2CH_3$, and —$OSO_2CF_3$. Suitable alkylating agents include alkyl halides (chlorides, bromides, or iodides), alkyl tosylates, alkyl mesylates, alkyl triflates, $\alpha,\beta$-unsaturated ketones, $\alpha,\beta$-unsaturated esters, $\alpha,\beta$-unsaturated aldehydes, $\alpha,\beta$-unsaturated amides, $\alpha,\beta$-unsaturated nitriles $\alpha,\beta$-unsaturated sulfones, and $\alpha,\beta$-unsaturated sulfonamides. Alkyl halides (e.g. iodides) are preferred. Suitable bases include triethylamine, sodium carbonate, sodium hydrogen carbonate, and sodium hydroxide. The preferred base is triethylamine. Suitable solvents include methylene chloride, chloroform, carbon tetrachloride, acetonitrile, tetrahydrofuran, diethyl ether, dioxane, N,N-dimethylformamide, N,N-dimethylacetamide, ethanol, propanol, methanol. The preferred solvent is acetonitrile. The reaction is conducted between a temperature of from about 0° C. to about 150° C, preferably from about 25° C. to about 65° C.

Compounds of formula III can be prepared by the Mitsunobu coupling reaction of compounds of formulas IV and V wherein W, n, m, $R_5$, $R_6$ (preferably bromide or iodide), and $R_7$ (preferably trifluoroacetyl [—$COCF_3$]) and $R_{11}$ are as defined above using a phosphine and an azodicarboxylate in an inert solvent. Suitable phosphines include trialkyl phosphines and triarylphosphines, preferably triphenylphosphine. Suitable azodicarboxylates include dialkyl azodicarboxylates, preferably diethyl diazodicarboxylate.

Compounds of formula IV can be prepared via the following reaction scheme:

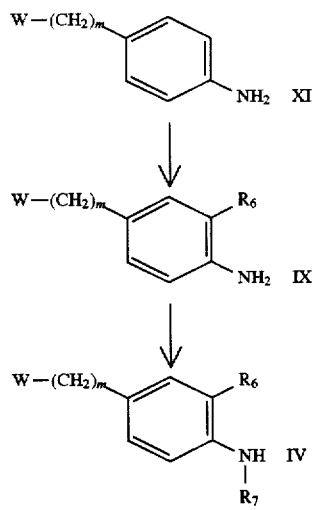

Compounds of formula IX can be prepared by reacting a compound of formula XI wherein W and m are as defined above with either chlorine, bromine, or iodine in an inert solvent with a base. Reaction with bromine is preferred. Suitable solvents include $C_1$ to $C_6$ alcohols, methylene chloride, chloroform, or carbon tetrachloride. The preferred solvent is methanol. Suitable bases include triethylamine, pyridine, sodium carbonate, and sodium hydrogen carbonate. The preferred base is sodium hydrogen carbonate. The reaction is conducted at a temperature of from about 0° C. to about 65° C., preferably at about 25° C.

Compounds of formula IV can be prepared by reacting a compound of formula IX wherein W, m, and $R_6$ are as defined above with the acid chloride or symmetrical anhydride of the formula $R_7OH$ in an inert solvent with a base. The preferred acid chloride or anhydride is trifluoroacetic anhydride. Suitable solvents include methylene chloride, chloroform as well as ethers, including tetrahydrofuran, diethyl ether and 1,4-dioxane. The preferred solvent is methylene chloride. Suitable bases include triethylamine, pyridine, and sodium hydrogen carbonate. The preferred base is pyridine. The reaction is conducted at a temperature of from about 0° C. to about 65° C., preferably at about 25° C.

Compounds of the formula XI can be prepared using methods known to one skilled in the art, such as, for example, as outlined in International Patent Application No. PCT/GB91/00908 and European Patent Application No. 313397A, both of which correspond to U.S. Pat. No. 5,225,431.

Compounds of the formula V can be prepared using the following reaction scheme:

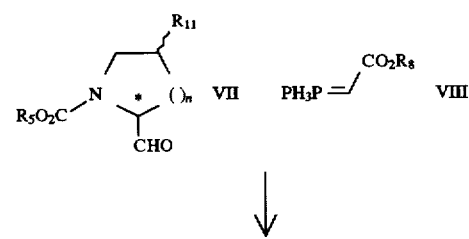

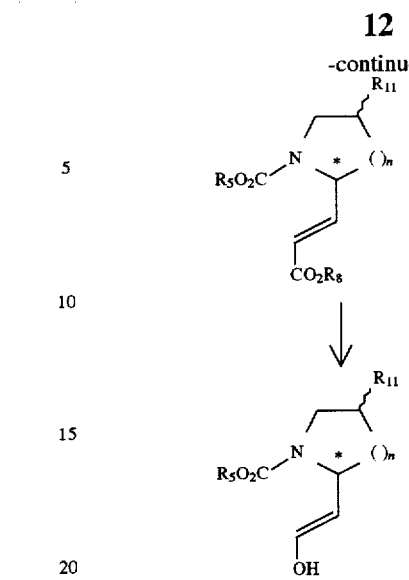

Compounds of the formula VI can be prepared using the Wittig reaction in an inert solvent involving compounds of the formulas VII and VIII wherein n, $R_5$, and $R_{11}$ are defined as above and $R_8$ is $C_1$ to $C_6$ alkyl, aryl, or $C_1$ to $C_3$ alkylaryl. Suitable solvents include ethers such a diethyl ether, tetrahydrofuran, and 1,4-dioxane. Tetrahydrofuran is the preferred solvent. The reaction is conducted at a temperature of from about -78° C. to about 80° C., preferably at about 25° C.

Compounds of the formula V can be prepared from a hydride reduction of a compound of formula VI wherein n, $R_5$, $R_8$, and $R_{11}$ are as defined above with a hydride reducing agent in an inert solvent. Suitable hydride reducing agents include lithium aluminum hydride, lithium borohydride, sodium borohydride, and diisobutylaluminum hydride. The preferred reagent is diisobutylaluminum hydride. Suitable solvents include ethers, such as diethyl ether, tetrahydrofuran, 1,4-dioxane and 1,2-dimethoxyethane. The preferred solvent is tetrahydrofuran. The reduction is conducted at a temperature of from about -100° C. to about 0° C., preferably from about -80° C. to about -70° C.

Compounds of the formula VII can be prepared using methods known in the art, such as, for example, as outlined in S. Kiyooka, et al., *J. Org. Chem.*, 5409 (1989) and Y. Hamada, et al., *Chem. Pharm. Bull.*, 1921 (1982).

Compounds of the formula VII are either commercially available or can be prepared using methods known in the art, such as, for example, as outlined in L. Fieser and M. Fieser, *Reagents for Organic Synthesis*, John Wiley and Sons, New York, Vol. 1, p. 112 (1967).

Compounds of formula I wherein W is (i), Z is O, m=1, $R_3$ and $R_2$ are each hydrogen may also be prepared via the following scheme:

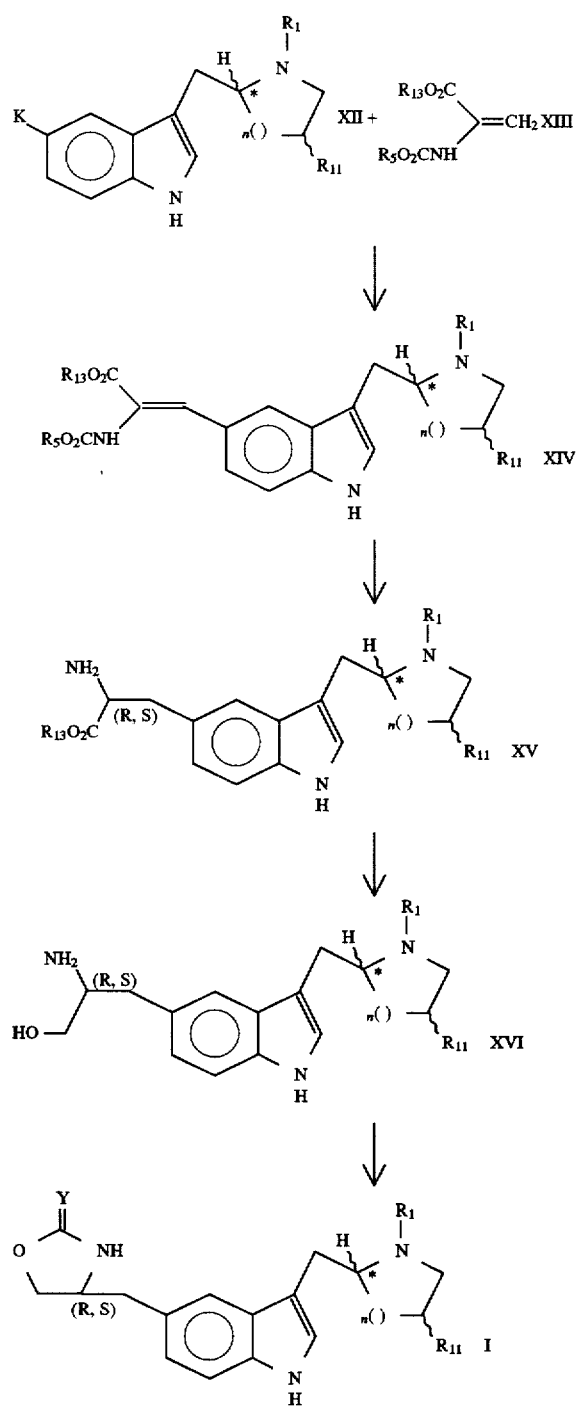

where W is (i), Z=O, m=1, $R_3$=H, $R_2$=H.

Compounds of formula XII, wherein n, $R_1$ and $R_{11}$ are as defined above and K is chloro, bromo or iodo (preferably bromo) can be prepared using methods known in the art, such as, for example, as described in WO 9206973.

Compounds of formula XIV, wherein n, $R_1$, $R_{11}$, and $R_5$ are as defined above and $R_{13}$ is $C_1$ to $C_6$ alkyl, aryl, or $C_1$ to $C_3$ alkylaryl, can be prepared by coupling a compound of formula XII with a dehydroalanine derivative of formula XIII wherein $R_5$ is as defined above (preferably benzyl) and $R_{13}$ is as defined above (preferably methyl), using the Heck reaction known in the art. Suitable palladium catalysts for the Heck reaction include palladium salts such as palladium (II) acetate, in the presence of a phosphine such as triphenylphosphine or tri-o-tolylphosphine, preferably tri-o-tolylphosphine. Suitable bases for the Heck reaction include trialkylamines, preferably triethylamine, and suitable inert solvents include acetonitrile and N,N-dimethylformamide, preferably acetonitrile. The reaction is conducted at a temperature of from about 60° C. to about 150° C., preferably at the reflux temperature of the solvent.

Compounds of formula XV, wherein $R_{13}$, $R_1$, $R_{11}$ and n are as defined above, can be prepared from compounds of formula XIV wherein $R_5$ is preferably benzyl, by catalytic reduction under an atmosphere of hydrogen, preferably at a pressure of from about 1 to about 3 atmospheres, or by using a hydrogen source such as ammonium formate or formic acid in an inert solvent. Suitable catalysts for either of the above reactions include palladium on carbon, Raney nickel and platinum oxide, preferably palladium on carbon. Suitable solvents for either of the above reactions include $C_1$ to $C_6$ alcohols, N,N-dimethylformamide, ethyl acetate and acetonitrile. The preferred solvent is ethanol. Optionally the reaction may be conducted in the presence of an acid. Suitable acids include hydrochloric acid. Suitable solvents for use with the acid include all those mentioned previously in this paragraph, preferably ethanol. All of these reactions are conducted at a temperature of from about 0° C. to about 60° C., preferably at about 25° C.

Compounds of formula XVI, wherein n, $R_1$, $R_{11}$ are as defined above, can be prepared from a compound of formula XV by reduction in an inert solvent. Suitable reducing agents include alkali metal borohydrides, such as sodium borohydride or lithium borohydride, or lithium aluminum hydrides such as lithium aluminum hydride. The preferred reducing agent is sodium borohydride. Suitable solvents for borohydride reducing agents include $C_1$ to $C_6$ alcohols, preferably ethanol. Suitable solvents for aluminum hydride reductions include ethers, such as tetrahydrofuran and diethyl ether, preferably tetrahydrofuran. The reaction is conducted at a temperature of from about 25° C. to about 80° C., preferably at the reflux temperature of the solvent.

Compounds of formula I, wherein W is (i), Z is O, m=1, $R^3$ and $R^2$ are each H and Y is as defined above, may be prepared by condensation of compounds of formula XVI with phosgene or a phosgene-equivalent in an inert solvent in the presence of a base. Suitable phosgene-equivalents where Y is O include N,N-carbonyldimidazole, diethyl carbonate and trichloromethyl chloroformate. The preferred reagent is phosgene itself. Suitable solvents include hydrocarbons or ethers, preferably toluene. Suitable bases include inorganic bases such as sodium hydroxide, potassium hydroxide and sodium carbonate. The reaction may also be carried out with suitable thio-phosgene equivalents where Y is S, such as N,N-thiocarbonyldiimidazole. The same reaction conditions used with phosgene are used with thiophosgene, as well.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, i.e., where $R_1$ contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium, magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction of maximum product of yields of the desired final product.

The compounds of the formula I and the pharmaceutically acceptable salts thereof (hereinafter, also referred to as the active compounds of the invention) are useful psychotherapeutics and are potent serotonin (5-$HT_1$) agonists and may be used in the treatment of depression, anxiety, eating disorders, obesity, drug abuse, cluster headache, migraine, chronic paroxysmal hemicrania and headache associated with vascular disorders, pain, and other disorders arising from deficient serotonergic neurotransmission. The compounds can also be used as centrally acting antihypertensives and vasodilators.

The active compounds of the invention can be evaluated as anti-migraine agents by testing the extent to which they mimic sumatriptan in contracting the dog isolated saphenous vein strip [P. P. A. Humphrey et al., Br. J. Pharmacol., 94, 1128 (1988)]. This effect can be blocked by methiothepin, a known serotonin antagonist. Sumatriptan is known to be useful in the treatment of migraine and produces a selective increase in carotid vascular resistance in the anesthetized dog. It has been suggested [W. Fenwick et al., Br. J. Pharmacol., 96, 83 (1989)] that this is the basis of its efficacy.

The serotonin 5-$HT_1$ agonist activity of the compounds of the present invention can be measured in in vitro receptor binding assays as described for the 5-$HT_{1A}$ receptor using rat cortex as the receptor source and [$^3$H]-8-OH-DPAT as the radioligand [D. Hoyer et al. Eur. J. Pharm., Vol. 118, 13 (1985)] and as described for the 5-$HT_{1D}$ receptor using bovine caudate as the receptor source and [$^3$H] serotonin as the radioligand [R. E. Heuring and S. J. Peroutka, J. Neuroscience, Vol. 7, 894 (1987)] 5-$HT_1$ agonist activity is defined by agents with affinities ($IC_{50}$'s) of 250 nM or less at either binding assay.

The compositions of the present invention may be formulated in a conventional manner using one or more pharmaceutically acceptable carriers. Thus, the active compounds of the invention may be formulated for oral, buccal, sublingual, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, methyl cellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

For buccal and sublingual administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult are preferably arranged so that each metered dose or "puff" of aerosol contains 20 µg to 1000 µg of the compound of the invention. The overall daily does with an aerosol will be within the range 100 µg to 10 mg. Administration may be several times daily, for example 2, 3, 4 or 8 times, giving for example, 1, 2 or 3 doses each time.

The following Examples illustrate how the compounds of the present invention can be prepared. Commercial reagents can be utilized without further purification. Room temperature refers to 20°–25° C.

EXAMPLE 1

General Procedure for the Alkylation of (R)-3-pyrrolidin-2-ylmethyl-1H-indoles

To a stirred solution of the (R)-3-(pyrrolidin-2-ylmethyl)-1H-indole (1.00 mmol) and triethylamine (0.126 g, 1.25 mmol, 1.25 eq) in either anhydrous methylene chloride, anhydrous acetonitrile, absolute ethanol, or i-propanol (10 mL) at room temperature under nitrogen is added dropwise the alkylating agent (1.25 mmol). The resulting reaction solution is then stirred under nitrogen at room temperature or heated at reflux for 1 to 20 hours, depending on substrate. The resulting reaction mixture is directly column chromatographed using silica gel (approximately 25 g) and elution with methylene chloride: methanol: ammonium hydroxide [9:1:0.1] to afford the title compound.

Using this procedure, the following compound was prepared:

3[(N-2-Methoxyethyl)pyrrolidin-2R-ylmethyl]-5-(2-oxo-1,3-oxazolidin-4S-ylmethyl)-1H-indole.

5-(2-Oxo-1,3-oxazolidin-4S-ylmethyl)-3-(pyrrolidin-2R-ylmethyl)-1H-indole and 2-bromoethyl methyl ether were used. Acetonitrile/ethanol (1:1) was the reaction solvent, and the reaction was heated at reflux for 3 hours. Column chromatography afforded the title compound (36%) as a light tan foam. $^{13}$C NMR (CD$_3$OD) δ 160.9, 135.9, 127.2, 126.3, 123.8, 123.1, 118.5, 111.3, 109.2, 69.1, 68.1, 67.6, 60.9, 57.8, 54.6, 53.8, 40.4, 29.5, 27.2, 21.3; [α]$^{25}$=+12°[c= 1, MeOH]; FAB LRMS (m/z, relative intensity) 359 (23), 358 (MH$^+$, 100), 188 (26); EI LRMS (m/z, relative intensity) 357 (0.1), 355 (2), 143 (25), 128 (100); HRMS calculated for C$_{20}$H$_{27}$N$_3$O$_3$, 357.2054 found 357.2062.

EXAMPLE 2

General Procedure for the Catalytic Reduction of 3-(N-Benzyloxycarbonyl-pyrrolidin-2-ylmethyl)-1H-indoles Forming 3-(Pyrrolidin-2-ylmethyl)-1H-indoles A mixture of the 3-(N-benzyloxycarbonylpyrrolidin-2-ylmethyl)-1H-indole (2.00 mmol) and 10% palladium on carbon (0.20 g) in absolute ethanol (15 mL) is shaken under a hydrogen atmosphere (3 atm) for 4 to 24 hours, depending on substrate. The resulting reaction mixture is filtered through diatomaceous earth, and the filtrate is evaporated under reduced pressure. The residue is column chromatographed using silica gel (approximately 50 g) and elution with a solution of methylene chloride: methanol: ammonium hydroxide [8:2:0.2] or other appropriate solvent system to afford the corresponding 3-(pyrrolidin-2-ylmethyl)-1H-indole.

Using this procedure, the following compound was prepared:

5-(2-Oxo-1,3-oxaolidin-4S-ylmethyl)-3-(pyrrolidin-2R-ylmethyl)-1H-indole.

3-(N-Benzyloxycarbonylpyrrolidin-2R-ylmethyl)-5-(2-oxo-1,3-oxazolidin-4S-ylmethyl)-1H-indole was used. Column chromatography afforded the title compound (89%) as an amorphous white solid: R$_f$=0.30 in methylene chloride/methanol/ammonium hydroxide [6:2:0.2]; $^1$H NMR (CD$_3$OD) δ7.43 (br s, 1H), 7.30 (d, J=8.3 Hz, 1H), 7.10 (s, 1H), 6.98 (dd, J=1.4 and 8.3 Hz, 1H), 4.90 (approximately 3H, exchangeable), 4.38–4.31 (m, 1H), 4.20–4.11 (m, 2H), 3.52–3.42 (m, 1H), 3.10–2.82 (m, 6H), 2.01–1.74 (m, 3H), 1.58–1.46 (m, 1H); $^{13}$C NMR (CD$_3$OD) δ 162.3, 137.3, 129.2, 127.5, 124.5, 124.0, 119.9, 112.8, 112.6, 70.7, 61.2, 47.0, 46.7, 42.2, 32.1, 31.1, 25.5; LRMS (m/z, relative intensity) 299 (3, M$^+$), 230 (31), 144 (18), 70 (100); HRMS calculated for C$_{17}$H$_{21}$N$_3$O$_2$ 299.1635, found 299.1628.

EXAMPLE 3

General Procedure for the Formation of 3-(Pyrrolidin-2-ylmethyl)-1H-indoles Via the Palladium Catalyzed Cyclization of 1-(N-Pyrrolidin-2-yl)-3-(N-(2-halophenyl)-N-trifluoroacetylamino)propenes A mixture of the 1-(pyrrolidin-2-yl)-3-(N-(2-halophenyl)-N-trifluoroacetylamino)propene (2.00 mmol), tetrabutylammonium chloride (2.00 mmol), and palladium(II) acetate (0.089 g, 0.40 mmol, 0.2 eq) in a solution of triethylamine (8 mL) and anhydrous N,N-dimethylformamide (4 mL) is heated at reflux under nitrogen for 2 hours. The resulting reaction mixture is evaporated under reduced pressure, and the residue is partitioned between ethyl acetate (25 mL) and water (25 mL). The ethyl acetate layer is removed, and the aqueous layer is extracted with ethyl acetate (25 mL). The organic extracts are combined, dried (MgSO$_4$), and evaporated under reduced pressure. The residue is column chromatographed using silica gel (approximately 50 g) and elution with an appropriate solvent system to afford the corresponding 3-(pyrrolidin-2-ylmethyl)-1H-indole.

Using this procedure, the following compound was prepared:

3-(N-Benzyloxycarbonylpyrrolidin-2R-ylmethyl)-5-(2-oxo-1,3-oxazolidin-4S-ylmethyl)-1H-indole.

1-(N-Benzyloxycarbonylpyrrolidin-2R-yl)-3-[N-(2-bromo-4-(2-oxo-1,3-oxazolidin-4S-ylmethyl) phenyl)-N-trifluoroacetylamino]propene was used. Column chromatography using 1:1 ethyl acetate/hexanes afforded the title compound (40%) as a clear, colorless oil: R$_f$=0.50 in ethyl acetate; LRMS (m/z, relative intensity) 433 (10, M$^+$), 298 (4), 229 (18), 204 (31), 160 (67), 143 (20), 91 (100); HRMS calculated for C$_{25}$H$_{27}$N$_3$O$_4$ 433.2003, found 433.2018.

EXAMPLE 4

General Procedure for the Formation 1-(Pyrrolidin-2-yl)-3-(N-(2-halophenyl)-N-trifluoroacetyamino) propenes from the Mitsunobu Coupling of 2-Halo-N-trifluoroacetylanilines with 1-(pyrrolidin-2-yl)-3-hydroxydropenes To a stirred solution of triphenylphosphine (0.655 g, 2.50 mmol, 1.25 eq) and diethyl azodicarboxylate (0.39 mL, 2.48 mmol, 1.25 eq) in anhydrous tetrahydrofuran (15 mL) at 0° C. under a nitrogen atmosphere is added dropwise a solution of the 2-halo-N-trifluoroacetylaniline (2.5 mmol, 1.25 eq) in anhydrous tetrahydrofuran (5 mL). This is then followed by the dropwise addition of a solution of 1-(pyrrolidin-2-yl)-3-hydroxypropene (R, or S, or racemate, 2.00 mmol) in anhydrous tetrahydrofuran (5 mL). The reaction solution is slowly warmed to 25° C. over the course of 2 hours, and then stirred at 25° C. under a nitrogen atmosphere for an additional 12 hours. The resulting reaction solution is evaporated under reduced pressure, and the residue is column chromatographed using silica gel (approximately 150 g) and elution with an appropriate solvent system to afford the corresponding 1-(pyrrolidin-2-yl)-3-(N-(2-halophenyl)-N-trifluoroacetyl-amino)propene.

Using this procedure, the following compound was prepared:

1-(N-Benzyloxycarbonylpyrrolidin-2R-yl)-3-[N-(2-bromo-4-(2-oxo-1,3-oxazolidin-4S-ylmethyl)phenyl)-N-trifluoroacetylamino]propene (R)-1-(N-Benzyloxycarbonylpyrrolidin-2-yl)-3-hydroxypropene and 2-bromo-4-(2-oxo-1,3-oxazolidin-4S-ylmethyl)-1-trifluoroactylaminobenzene were used. Column chromatography afforded the title compound (100%) as a clear, colorless oil; $R_f$=0.45 in ethyl acetate; FAB LRMS (m/z, relative intensity) 612 (5, [MH$^+$ with $^{81}$Br]), 610 (8, [MH$^+$ with $^{79}$Br]), 568 (5), 566 (8), 502 (3), 476 (4), 279 (100); HRMS calculated for $C_{27}H_{27}BrF_3N_3O_5$ 609.1087, found 609.0952.

EXAMPLE 5

(R)-3-Hydroxy-1-(N-methylpyrrolidin-2-yl)propene

To a stirred solution of lithium aluminum hydride (0.73 g, 19.24 mmol, 2.2 equivalents) in anhydrous tetrahydrofuran (20 mL) at 0° C. was added dropwise a solution of (R)-1-(N-benzyloxycarbonylpyrrolidin-2-yl)-3-hydroxypropene (2.30 g, 8.80 mmol) in anhydrous tetrahydrofuran (20 mL). The resulting reaction mixture was heated at reflux under nitrogen for 3.5 hours. The resulting mixture was then cooled, and sodium sulfate decahydrate (10 g) was added slowly with caution. This mixture was stirred at room temperature under nitrogen for 1 hour, and then ethyl acetate (100 mL) and water (1 mL) was added. The resulting mixture was stirred at room temperature under nitrogen overnight. The mixture was then filtered through Celite®, and the filtrate was evaporated under reduced pressure. Column chromatography of the residual oil using silica gel (approximately 200 g) and elution with methylene chloride/methanol/ammonium hydroxide (9:1:0.1) afforded the title compound (1.13 g, 8.00 mmol, 91%) as a clear, colorless liquid: $^{13}$C NMR (CDCl$_3$) δ 132.6, 132.5, 69.0, 62.7, 56.6, 40.2, 31.8, 22.1; Anal. calcd for $C_8H_{15}NO$·0.175 $H_5NO$ [ammonium hydroxide]: C, 65.21; H, 10.88; N, 11.34. Found: C, 65.01; H, 10.71; N, 10.81.

EXAMPLE 6

(R)-1-(N-Benzyloxycarbonylpyrrolidin-2-yl)-3-hydroxypropene

To a stirred solution of ethyl (R)-3-(N-benzyloxycarbonylpyrrolidin-2-yl)-2-propenoate (3.03 g, 10.00 mmol) in anhydrous tetrahydrofuran (75 mL) at −78° C. under nitrogen was added dropwise a solution of diisobutylaluminum hydride (1.0M in hexanes, 22.0 mL, 22.0 mmol, 2.2 eq). The resulting solution was stirred at −78° C. under nitrogen for 30 minutes. The reaction solution was then allowed to warm to room temperature over the course of 2 hours. A saturated solution of sodium hydrogen carbonate (50 mL) was added, and the aqueous mixture was extracted with ethyl acetate (3×50 mL). The extracts were combined, dried (MgSO$_4$), and evaporated under reduced pressure. Column chromatography of the residue with diethyl ether/hexanes [1:1] afforded the title compound as a clear colorless oil (1.41 g, 5.40 mmol, 54%): $^1$H NMR (CDCl$_3$) δ 7.40–7.25 (m, 5H), 5.75–5.53 (m, 2H), 5.20–5.00 (m, 2H), 4.38 (br m, 1H), 4.06 (br d, J=13.7Hz, 2H), 3.45 (br t, J=7.0 Hz, 1H), 2.03–1.68 (m, 4H); $[\alpha]^{25}$=+34° (MeOH, c=1.0); HRMS calculated for $C_{15}H_{19}NO_3$ 261.1365, found 261.1356.

EXAMPLE 7

Ethyl (R)-3-(N-Benzyloxycarbonylpyrrolidin-2-yl)-2-propenoate

To a stirred solution of N-carbobenzyloxypyrrolidine-2-carboxaldehyde (1.17 g, 5.00 mmol) in anhydrous tetrahydrofuran at −78° C. was added (carboethoxymethylene)-tripphenylphosphorane (2.09 g, 6.00 mmol, 1.2 eq) as a solid portionwise. The resulting reaction mixture was stirred at room temperature under nitrogen for 2 hours, and then heated at reflux under nitrogen for 1 hour. The reaction mixture was evaporated under reduced pressure and the residue was column chromatographed using silica gel (approximately 100 g) and elution with 20% diethyl ether in hexanes to afford the title compound as a clear, colorless oil (1.11 g, 3.65 mmol, 73%): $^1$H NMR (CDCl$_3$-d$_6$) δ 7.34–7.25 (m, 5H), 6.89–6.76 (m, 1H), 5.88–5.74 (m, 1H), 5.18–5.05 (m, 2H), 4.60–4.43 (m, 1H), 4.17 (q, J=7.1 Hz, 2H), 3.55–3.40 (m, 2H), 2.11–2.00 (m, 1H), 1.90–1.75 (m, 3H), 1.28 (t, J=7.1 Hz, 3H); $^{13}$C NMR (CDCl$_3$) [Note: due to slow nitrogen inversion two conformers of the products are seen by NMR spectroscopy] δ 166.3, 154.7, 147.9, 147.4, 136.6, 128.4, 127.9, 120.9, 66.9, 65.8, 60.4, 58.1, 57.7, 46.8, 46.4, 31.6, 30.8, 23.6, 22.8, 22.6, 15.3, 14.2.

EXAMPLE 8

General Synthesis of 2-Halo-N-trifluoroacetylanilines

To a stirred mixture of the N-trifluoroacetylaniline (2.00 mmol) and sodium hydrogen carbonate (0.21 g, 2.50 mmol, 1.25 eq) in methanol (10 mL) at 0° C. is added dropwise bromine (0.113 mL, 2.19 mmol, 1.1 eq). The resulting reaction mixture is then stirred at 25° C. for 30 minutes. The reaction mixture is then evaporated under reduced pressure, and the residue is placed in water made acidic to pH 3 with HCl (10 mL). This aqueous mixture is extracted with ethyl acetate (3×15 mL). The extracts is combined, dried (MgSO$_4$), and evaporated under reduced pressure. The residue is column chromatographed using silica gel (approximately 50 g) and elution with an appropriate solvent system to afford the corresponding 2-bromo-N-trifluoroacetylaniline.

Using this procedure, the following compound was prepared:

2-Bromo-4-(2-oxo-1,3-oxazolidin-4S-ylmethyl)-1-trifluoroacetylaminobenzene 4-(2-Oxo-1,3-oxazolidin-4S-ylmethyl)-1-trifluoroacetylaminobenzene was used. Column chromatography using 7% acetone in methylene chloride afforded the title compound (45%) as a white solid: mp 157.0°–160.0°

C., $^{13}$C NMR (acetone-d$_6$) δ 159.3, 139.5, 134.6, 132.9, 130.3, 128.1, 119.9, 118.8, 115.0, 69.4, 53.7, 40.7; [α]$^{25}$=−28° (MeOH, c=1); HRMS calculated for C$_{12}$H$_{10}$BrF$_3$N$_2$O$_3$ 356.9827, found 365.9824.

EXAMPLE 9

General Synthesis of N-trifluoroacetylaminobenzenes

To a stirred solution of the aniline (2.00 mmol) and pyridine (0.18 mL, 2.22 mmol, 1.1 eq) in anhydrous methylene chloride (10 mL) at 0° C. under a nitrogen atmosphere is added dropwise trifluoroacetic anhydride (0.31 mL, 2.19 mmol, 1.1 eq). The resultant reaction mixture is stirred at 0° C. under a nitrogen atmosphere for 3 hours. Water is added (15 mL), and this aqueous mixture is extracted with ethyl acetate (3×15 mL). The extracts are combined, dried (mgSO$_4$), and evaporated under reduced pressure. If necessary, the residue is column chromatographed using silica gel (approximately 50 g) and elution with an ethyl acetate gradient in hexanes to afford the corresponding N-trifluoroacetylaminobenzene.

Using this procedure the following compound was prepared:

4-(2-Oxo-1,3-oxazolidin-4S-ylmethyl)-1-trifluoroacetylaminobenzene 4-(2-Oxo-1,3-oxazolidin-4S-ylmethyl)-1-aminobenzene (WO 91/18897) was used. Column chromatography using 1:1 ethyl acetate/hexanes followed by ethyl acetate afforded the title compound (70%) as a white, crystalline solid: mp 132.0°–136.0° C.; R$_f$ =0.35 in ethyl acetate; [α]$^{25}$=−14° (MeOH, c=1); Anal. calcd for C$_{12}$H$_{11}$N$_2$F$_3$O$_3$; C, 50.01; H, 3.85; N, 9.72. Found: C, 50.29; H, 3.81; N, 9.67.

EXAMPLE 10

5-(2-Benzyloxycarbonylamino-2-methoxycarbonylethen-1-yl)-3-(N-methylpyrrolidin-2R-ylmethyl)-1H-indole 5-Bromo-3(N-methylpyrrolidin-2R-ylmethyl)-1H-indole (4.65 g, 15.9 mmol), N-benzyloxycarbonyl-dehydroalanine methyl ester (5.0 g, 21.3 mmol), tri-o-tolyl phosphine (1.4 g, 4.6 mmol), palladium (II) acetate (350 mg, 1.6 mmol) and triethylamine (4.7 mL, 33.8 mmol) were dissolved in acetonitrile (50 mL) and heated at reflux with stirring under nitrogen overnight. After cooling to room temperature, the reaction mixture was partitioned between ethyl acetate and 2M aqueous sodium carbonate. The organic phase was washed with brine, dried (Na$_2$SO$_4$) and evaporated under reduced pressure. The resulting residue was purified by column chromatography on silica gel, eluting with a gradient of dichloromethane: ethanol (100:0 to 80:15), to yield 1.4 g of the title compound as a foam: R$_f$=0.3 dichloromethane: methanol: 0.880 aqueous ammonia (90:10:1); $^1$H NMR (CDCl$_3$) δ 8.35 (br s, 1H), 7.80 (s, 1H), 7.56 (s, 1H), 7.50 (d, 1H), 7.40–7.28 (m, 6H), 7.04 (d, 1H), 6.40 (br s, 1H), 5.30 (s, 0.2H, CH$_2$Cl$_2$), 5.20–5.06 (m, 2H), 3.90–3.75 (br s, 3H), 3.28–3.14 (m, 2H), 2.75–2.45 (m, 5H), 2.32–2.20 (m, 1H), 1.90–154 (m, 4H). Anal. calcd for C$_{26}$H$_{29}$N$_3$O$_4$·0.1 CH$_2$Cl$_2$·0.25:H$_2$O: C, 68.07; H, 6.50; N, 9.12. Found: C, 67.94; H, 6.51; N; 9.29.

EXAMPLE 11

5-(2R,S-Amino-2-methoxycarbonylethyl)-3-(N-methylpyrrolidin-2(R)-ylmethyl)-1H-indole 5-(2-Benzyloxycarbonylamino-2-methoxycarbonylethen-1-yl)-3-(N-methylpyrrolidin-2R-ylmethyl)-1H-indole (150 mg, 0.34 mmol) was dissolved in ethanolic hydrogen chloride (prepared from ethanol (4 mL) and acetyl chloride (0.048 ml, 0.68 mmol)) and the resulting solution was hydrogenated over 10% palladium-on-carbon (100 mg) at room temperature at a pressure of hydrogen of 15 psi overnight. The reaction mixture was filtered through a pad of Arbacell and evaporated under reduced pressure. The residue was partitioned between ethyl acetate and 2M aqueous sodium carbonate, the aqueous phase reextracted with ethyl acetate and the combined organic phases washed with brine, dried (Na$_2$SO$_4$) and evaporated under reduced pressure. The resulting residue was purified by column chromatography on silica gel, eluting with dichloromethane: ethanol gradient (90:10 to 80:20), followed by a gradient of dichloromethane: methanol : 0.880 aqueous ammonia (80:20:0 to 80:20:1), yielding 60 mg of the title compound as a gum: R$_f$=0.2 dichloromethane: methanol : 0.880 aqueous ammonia (90:10:1); [α]$_D^{25}$ +73° (c=0.1, CH$_3$OH); $^1$H NMR (CDCl$_3$) δ 8.78 (br s, 1H), 7.37 (s, 1H), 7.24 (d, 1H), 7.00–6.95 (m, 2H), 5.28 (s, 0.2H, CH$_2$Cl$_2$), 3.82–3.78 (m, 1H), 3.72 (s, 3H), 3.25–3.18 (m, 3H), 3.00–2.92 (m, 1H), 2.62–2.56 (m, 1H), 2.5–2.4 (m, 4H), 2.28–2.18 (m, 1H), 1.9–1.5 (m, 6H). Anal. calc'd for C$_{18}$H$_{25}$N$_3$O$_2$·0.1 CH$_2$Cl$_2$: C, 67.11; H, 7.84; N, 12.97. Found: C, 67.57; H, 7.90; N, 12.77.

EXAMPLE 12

5-(2R,S-Amino-3-hydroxyprop-1-yl)-3-(N-methylpyrrolidin-2R-ylmethyl)-1H-indole 5-(2R,S-Amino-2-methoxycarbonylethyl)-3-(N-methylpyrrolidin-2R-ylmethyl)-1H-indole (0.57 g, 1.8 mmol) was dissolved in ethanol (2.5 mL) and water (2.5 mL) and the resulting solution was added slowly to a stirred suspension of sodium borohydride (72 mg, 1.9 mmol) in water (2.5 mL) and ethanol (2.5 mL) at 0° C. The solution was heated at reflux for 3 hours and cooled to room temperature. After evaporation under reduced pressure, the resulting residue was extracted with dichloromethane (8×30 mL), the extract filtered to remove solid material, and the filtrate was evaporated under reduced pressure. The resulting residue was azeotroped with dichloromethane (2x) to yield 130 mg of the title compound as a white foam: R$_f$=0.1 dichloromethane: ethanol : 0.880 aqueous ammonia (25:8:1); $^1$H NMR (CDCl$_3$) δ 8.02 (br s, 1H), 7.38 (s, 1H), 7.30 (d, 1H), 7.03–7.00 (m, 2H), 5.30 (s, 0.66H, CH$_2$Cl$_2$), 3.70–3.65 (m, 1H), 3.44–3.38 (m, 1H), 3.20–3.10 (m, 3H), 2.95–2.88 (m, 1H), 2.70–2.55 (m, 2H), 2.50–2.38 (m, 4H), 2.26–2.18 (m, 1H), 1.90–1.00 (m, 7H). Anal. calcd for C$_{17}$H$_{25}$N$_3$O·0.33 CH$_2$Cl$_2$: C, 65.94; H, 8.19; N, 13.31. Found: C, 65.75; H, 8.28; N, 12.93.

EXAMPLE 13

5-(2-Oxo-1,3-oxaolidin-4R,S-ylmethyl)-3-(N-methylpyrrolidin-2R-ylmethyl)-1H-indole 5-(2R,S-Amino-3-hydroxyprop-1-yl)-3-(N-methylpyrrolidin-2R-ylmethyl)-1H-indole (50 mg, 0.17 mmol) was dissolved in toluene (2.5 mL). Potassium hydroxide (50 mg) was dissolved in water (0.8 mL) and this solution added to the above toluene solution. The resultant mixture was cooled (ice-bath) and a solution of phosgene in toluene (12.5%, 0.56 mL) was added with stirring. After cooling with an ice-bath for 15 minutes, the reaction was stirred at room temperature overnight. The organic phase was separated, the aqueous layer extracted with ethyl acetate and then dichloromethane, and all organic phases were evaporated under reduced pressure, to yield a white foam.

Purification by column chromatography on silica gel, eluting with dichloromethane followed by a gradient of dichloromethane : methanol : 0.880 aqueous ammonia (90:10:1 to 70:30:2), yielded 15 mg of the title compound: $R_f$=0.7 in dichloromethane: methanol: 0.880 aqueous ammonia (70:30:2); $^1$H NMR (CDCl$_3$) δ 8.35 (br s, 1H), 7.40–7.28 (m, 2H), 7.05 (s, 1H), 6.96 (d, 1H), 5.42 (br d, 1H), 5.30 (s, 1H, CH$_2$Cl$_2$), 4.50–4.42 (m, 1H), 4.22–4.14 (m, 2H), 3.22–3.15 (m, 2H), 3.02–2.88 (m, 2H), 2.75–2.40 (m, 5), 2.35–2.20 (m, 1H), 1.90–1.50 (m, 4H). Anal. calcd for $C_{18}H_{23}N_3O_2 \cdot 0.5$ CH$_2$Cl$_2$: C62.43; H, 6.80; N, 11.81. Found: C, 62.66; H, 6.26; N, 11.71.

We claim:

1. A compound of the formula

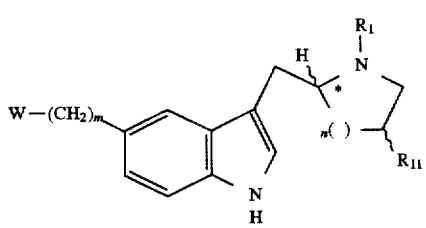

where W is

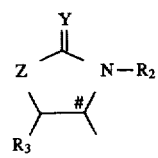 (i)

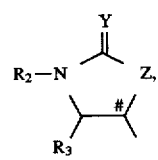 (ii)

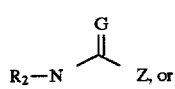 (vi)

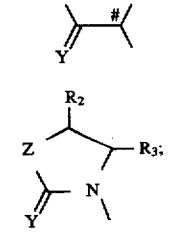 (vii)

n is 0 or 1; m is 0, 1, 2, or 3; Y and G are each independently oxygen or sulfur; Z is —O—; $R_1$ is hydrogen, $C_1$ to $C_8$ alkyl, substituted $C_1$ to $C_8$ alkyl substituted with one hydroxy, $C_3$ to $C_8$ alkenyl, $C_3$ to $C_8$ alkynyl, aryl, $C_1$ to $C_3$ alkylaryl, or —Q—R$_4$; $R_2$ and $R_3$ are each independently hydrogen, $C_1$ to $C_6$ alkyl, aryl, or $C_1$ to $C_3$ alkylaryl; $R_4$ is cyano, trifluoromethyl, —COR$_9$, —CO$_2$R$_9$, —CONR$_9$R$_{10}$, —OR$_9$, —SO$_2$NR$_9$R$_{10}$, or —S(O)$_q$R$_9$; $R_9$ and $R_{10}$ are each independently hydrogen, $C_1$ to $C_8$ alkyl, $C_1$ to $C_3$ alkylaryl, aryl, or $R_9$ and $R_{10}$ may together be taken to form a three- to seven-membered alkyl ring or a three- to seven-membered heteroalkyl ring having 1 heteroatom of O; Q is $C_1$ to $C_3$ alkyl; $R_{11}$ is hydrogen, —OR$_{12}$, or —NHCOR$_{12}$; $R_{12}$ is hydrogen, $C_1$ to $C_6$ alkyl, aryl, or $C_1$ to $C_3$ alkyl-aryl; q is 0, 1, or 2; a first chiral carbon is designated by an asterisk; a second chiral carbon is designated by #; the above alkyl, alkenyl, alkynyl, and alkylene moieties of other groups are linear, branched, cyclic, or be linear or branched and containing cyclic moieties; and the above aryl groups and the aryl moieties of the above alkyl-aryl groups are independently selected from phenyl and substituted phenyl, wherein said substituted phenyl may be substituted with one nitro or one to three groups selected from $C_1$ to $C_4$ alkyl, halogen, hydroxy, cyano, carboxamido, and $C_1$ to $C_4$ alkoxy and the pharmaceutically acceptable salts thereof.

2. The compound of claim 1, wherein the compound of formula I is

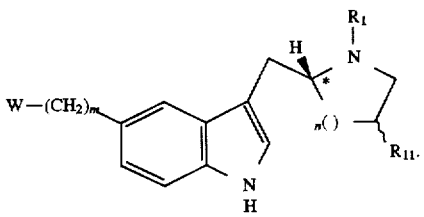

3. The compound of claim 2, wherein the compound is the cis epimer.

4. The compound of claim 1, wherein the compound of formula I is the S epimer having the chiral carbon designated by #.

5. The compound of claim 1, wherein G is oxygen.

6. The compound of claim 1, wherein W is (i), (ii), (iii), or (iv); $R_1$ is hydrogen, $C_1$ to $C_6$ alkyl, aryl, $C_1$ to $C_3$ alkylaryl, $C_1$ to $C_3$ alkylheteroaryl, or —Q—R$_4$; and R$_4$ is cyano, trifluoromethyl, —CO$_2$CH$_3$, —CONH$_2$, —OH, —OCH$_3$, or —O-phenyl.

7. The compound of claim 6, wherein the compound of formula I is

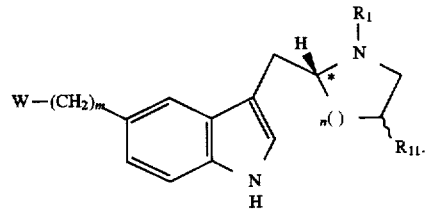

8. The compound of claim 7, wherein the compound is the cis epimer.

9. The compound of claim 6, wherein the compound of formula I is the S epimer having the chiral carbon designated by #.

10. The compound of claim 1, wherein W is (i), (ii), or (iii); n is 1; m is 1; $R_1$ is hydrogen, $C_1$ to $C_3$ alkyl, or —CH$_2$CH$_2$OCH$_3$; $R_2$ is hydrogen; and $R_3$ is hydrogen or —CH$_2$Ph.

11. The compound of claim 10, wherein the compound of formula I is

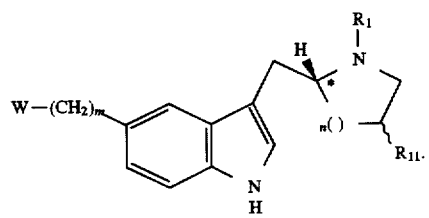

12. The compound of claim 11, wherein the compound is the cis epimer.

13. The compound of claim 10, wherein the compound of formula I is the S epimer having the chiral carbon designated by #.

14. The compound of claim 1, said compound being selected from

3-[(N-2-Methoxyethyl)pyrrolidin-2R-ylmethyl]-5-(2-oxo-1,3-oxazolidin-4S-ylmethyl)-1H-indole;

5-(2-Oxo-1,3-oxazolidin-4S-ylmethyl)-3-(pyrrolidin-2R-ylmethyl)-1H-indole; and 3-(N-Methylpyrrolidin-2R-ylmethyl)-5-(2-oxo-1,3-oxazolidin-4R,S-ylmethyl)-1H-indole.

15. A pharmaceutical composition for treating a condition selected from hypertension, depression, anxiety, eating disorders, obesity, drug abuse, cluster headache, migraine, pain, and chronic paroxysmal hemicrania and headache associated with vascular disorders comprising an amount of a compound according to claim 1 effective in treating such condition and a pharmaceutically acceptable carrier.

16. A pharmaceutical composition for treating disorders arising from deficient serotonergic neurotransmission comprising an amount of a compound according to claim 1 effective in treating such a disorder and a pharmaceutically acceptable carrier.

17. A method for treating a condition selected from hypertension, depression, anxiety, eating disorders, obesity, drug abuse, cluster headache, migraine, pain, and chronic paroxysmal hemicrania and headache associated with vascular disorders comprising administering to a mammal requiring such treatment an amount of a compound according to claim 1 effective in treating such condition.

18. A compound of the formula

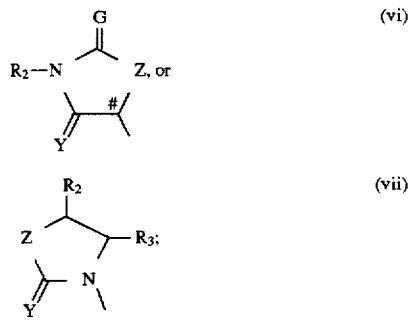

(II)

where W is

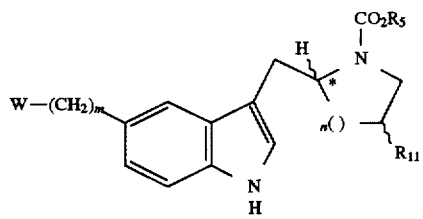

(i)

(ii)

-continued

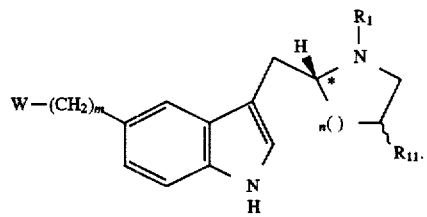

(vi)

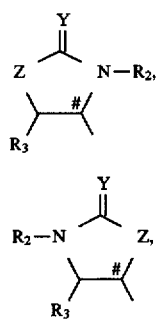

(vii)

n is 0 or 1; m is 0, 1, 2, or 3; Y and G are each independently oxygen or sulfur; Z is —O—; $R_2$ and $R_3$ are each independently hydrogen, $C_1$ to $C_6$ alkyl, aryl, or $C_1$ to $C_3$ alkylaryl; $R_5$ is $C_1$ to $C_6$ alkyl, aryl, or $C_1$ to $C_3$ alkylaryl; $R_{11}$ is hydrogen, —$OR_{12}$, or —$NHCOR_{12}$; $R_{12}$ is hydrogen, $C_1$ to $C_6$ alkyl, aryl, or $C_1$ to $C_3$ alkyl-aryl; a first chiral carbon is designated by an asterisk; a second chiral carbon is designated by #; the above alkyl and alkylene moieties of other groups are linear, branched, cyclic, or be linear or branched and containing cyclic moieties; and the above aryl groups and the aryl moieties of the above alkyl-aryl groups are independently selected from phenyl and substituted phenyl, wherein said substituted phenyl may be substituted with one nitro or one to three groups selected from $C_1$ to $C_4$ alkyl, halogen, hydroxy, cyano, carboxamido, and $C_1$ to $C_4$ alkoxy.

19. The compound of claim 18, wherein the compound of formula II is

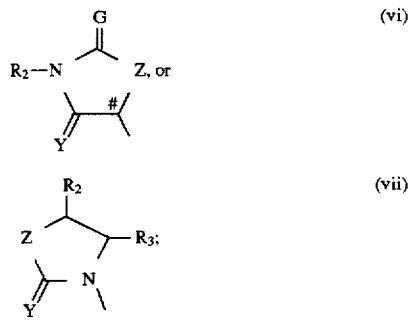

20. The compound of claim 19, wherein the compound is the cis epimer.

21. The compound of claim 18, wherein the compound of formula II is the S epimer having the chiral carbon designated by #.

22. The compound of claim 18, wherein G is oxygen.

* * * * *